United States Patent
Shtakelberg et al.

(10) Patent No.: US 7,181,978 B2
(45) Date of Patent: Feb. 27, 2007

(54) METHOD, APPARATUS AND SYSTEM FOR FORECASTING STRENGTH OF CEMENTITIOUS MATERIAL

(75) Inventors: David Shtakelberg, Jerusalem (IL); Boris Wilge, Doar Na Merkaz (IL); Shimon Boiko, Har Adar (IL)

(73) Assignee: Concretec Ltd., Jerusalem (IL)

( * ) Notice: Subject to any disclaimer, the term of this patent is extended or adjusted under 35 U.S.C. 154(b) by 109 days.

(21) Appl. No.: 10/793,750

(22) Filed: Mar. 8, 2004

(65) Prior Publication Data

US 2005/0103119 A1    May 19, 2005

Related U.S. Application Data

(60) Provisional application No. 60/519,653, filed on Nov. 14, 2003.

(51) Int. Cl.
    *G01N 3/00*    (2006.01)
(52) U.S. Cl. .................................................... 73/803
(58) Field of Classification Search ................... 73/803
    See application file for complete search history.

(56) References Cited

U.S. PATENT DOCUMENTS

| 3,974,679 | A | * | 8/1976 | Nasser ........................ 73/803 |
| 4,159,640 | A | * | 7/1979 | Leveque et al. ............... 73/81 |
| 4,182,191 | A | * | 1/1980 | Ikeda ........................... 73/803 |
| 4,259,868 | A | * | 4/1981 | Rao et al. ..................... 73/597 |
| 4,802,145 | A | * | 1/1989 | Mount II ...................... 367/35 |
| 5,041,987 | A | * | 8/1991 | Kuwahara et al. ............ 73/803 |
| 5,627,368 | A | * | 5/1997 | Moake .................... 250/269.3 |
| 6,023,170 | A | * | 2/2000 | Hilhorst et al. ............. 324/689 |
| 6,396,265 | B1 | * | 5/2002 | Shtakelberg et al. ........ 324/300 |
| 6,675,895 | B1 | * | 1/2004 | Shehab et al. .............. 166/292 |

* cited by examiner

*Primary Examiner*—Max Noori

(57) ABSTRACT

A method of forecasting strength of a chemically active material while hardening is disclosed. The chemically active material is characterized by at least one physical parameter. The method comprises: (a) measuring the at least one physical parameter over a predetermined time-interval, so as to obtain at least one series of measurements; (b) extracting a predetermined time-dependence of the at least one physical parameter over at least a portion of the predetermined time-interval; and (c) using the predetermined time-dependence of the at least one physical parameter to forecast the strength of the chemically active material at a future time.

97 Claims, 6 Drawing Sheets

METHOD, APPARATUS AND SYSTEM FOR FORECASTING STRENGTH OF CEMENTITIOUS MATERIAL

This Application claims the benefit of priority from U.S. Provisional Patent Application No. 60/519,653, filed Nov. 14, 2003, the contents of which are hereby incorporated by reference.

FIELD AND BACKGROUND OF THE INVENTION

The present invention relates to a method, apparatus and system for forecasting strength of chemically active materials while hardening, and, more particularly, to a method, apparatus and system for non-destructive forecasting of concrete strength.

As used herein throughout the specification and in the claims section below, the phrase "chemically active material(s)" includes cementitious materials, such as, but not limited to, cement paste, mortar, concrete, lime, gypsum, clay and the like that undergo a curing process when hardening.

A chemically active material often needs to be analyzed so as to determine the structural properties parameters, particularly strength and other physical-mechanical properties of the final cured product, such as its potential for shrinkage. The final strength of a chemically active capillary-porous material is determined by the mixing and compacting conditions, and by its specific composition such as, but not limited to, mineral binder-to-aggregate ratio, water-to-cement, water-to-aggregate ratio and the like [Neville A. M., "Properties of concrete," Longman Scientific & Technical, 1981].

The hardening process of a chemically active material consists of several stages, each characterized by a different combination between the liquid phase and the solid phase of the material.

FIGS. 1a–b show a typical strength curve of a cement of type CEM-1 Portland (42.5N), according to the European Standard EN-197, Part 1: "Composition, specifications and conformity criteria for common cements." FIGS. 1a–b show the compressive strength, R, of the cement in Megapascals (MPa), as a function of time, t, in a linear (FIG. 1a) and a logarithmic (FIG. 1b) time scale.

Generally, the hardening process is as follows [Powers T. C. and Brownyard T. L., "Studies of the physical properties of hardened Portland cement paste" (9 parts), Journ. Amer. Concr. Inst., 43 (October 1946 to April 1947); Shtakelberg D. I. and Sithcov M. M., "Self-organization in disperse systems," Riga, "Zinatne" Press, 1990]. Immediately following the mixing and compaction of the cement, the material typically has a long-range coagulation structure. This long-range coagulation structure gradually changes to a short range coagulation structure in which a colloid capillary-porous body is formed. At this stage the liquid phase of the structure is continuous, while the solid phase is discrete. The solid particles present in the material interact through the intermediating liquid and the mechanical stability of the structure is determined by the compressive action of capillary menisci.

Due to the accumulation of reaction products, the concentration of the solid phase increases, disturbing the continuity of the liquid phase, thus forming a structure characterized by a discrete liquid phase and a discrete solid phase. The discretization of the liquid phase is accompanied by an ongoing crystallization processes in which solid-phase contacts appear in the places where the liquid phase is disrupted, first as coagulation type contacts and thereafter as crystalline type contacts. As a result of the formation of crystalline type contacts, the strength of the material is significantly increased.

In the final stage of hardening, the concentration of crystalline type contacts continue to increase until a continuous crystalline frame is formed. The material in this stage is characterized by continues solid phase and a discrete liquid phase.

Traditional prior art methods for testing the strength of concrete typically require 28 days to complete. The builder usually does not or cannot delay construction 28 days to receive the test results. Rather, the construction usually continues in the hope that the concrete is sound. If in the final analysis, the concrete does not meet the standards, the building may have to be reinforced or even torn down, perhaps incurring major additional costs.

Improvements in cement production and prediction of concrete performance properties require the application of material science. Methods of predicting the final strength of concrete while hardening have been developed over the years, based on theoretical and experimental investigations of the crystallization strengthening laws and the properties of chemically active material [to this end see, e.g., Abrams D. A. "Design of concrete mixtures," Bull. No. 1, Sruct. Mater. Lab., Lewis Inst., Chicago, 1918; Powers T. C., "Structure and physical properties of hardened Portland cement paste," J. Amer. Ceramic. Soc., 41, 1958, pp. 1–6; Roy D. M. and Gouda G. R., "Porosity-strength relation in cementitious materials with very high strength," J. Amer. Ceramic. Soc., 53, No. 10, 1973, pp. 549–550; Sheikin A. E., Chekhovsky I. V. and Brusser M. I., "Structure and properties of cementitious concrete," Stroyizdat Press, Moscow, 1973 (in Russian)].

It has been established that the strength, R, of a chemically active material is determined by the following strength-porosity power-law:

$$R = A * P^m, \qquad (EQ. 1)$$

where P is the porosity of the material, and A and m are constants.

Equation 1 is applicable only within the limited domain of the crystalline state of the material, only after the material experiences the aforementioned structure conditions. In the second hardening stage, the crystalline properties of the body are predominant. Denoting the initial (zero) mechanical strength of the material by $R_{cr(0)}$, an estimation of the strength of the material 28 days after its mixing can be calculated using Equation 2, below:

$$R_{28} = R_{cr(0)} \frac{\log 28}{\log n}, \qquad (EQ. 2)$$

where: n denotes the age of the material (in days) at the time where the initial strength $R_{cr(0)}$ is reached.

One method to predict the concrete strength [King J. W. H., "Further notes on the accelerated test for concrete," Chartered Civil Engineer, London, May 1957, pp. 15–19] is based just on Equations 1 and 2 above. The essence of the method consists in accelerated determination of the strength of concrete warmed up to 200° F. (93° C.) and aged 6 hours with subsequent extrapolation of the obtained results and strength correlation for the 7-day and 28-day age.

Also known [Y. Ono, "Microscopic observation of clinker for estimation of burning condition, grindability and hydraulic activity," Proc. $3^d$ Intern. Conf. Cem. Microscopy, Houston, 1981] are attempts to predict the 28-day strength of cement proceeding from the measurement results of Portland cement clinker crystals by means of an electronic microscope, using the following empirical formula:

$$R(kgf/cm^2)=253+6.4AS+21.9AB+4.0BS+21.5BC, \quad (EQ. 3)$$

where AS is the size of alite crystals, AB is the birefringence of alite, BS is the size of belite crystals and BC is the color of belite.

In an additional method [Sinha S. K., Rao L. H. and Akhouri P. H., "Rapid estimation of the 28-day compressive strength of clinker by optical microscopy," Proc. $13^{th}$ Intern. Conf. Cem. Microscopy. ICMA, Florida, April 1991], the 28-day strength of cement is determined by the following empirical formula:

$$R(kgf/cm^2)=81.6+7.5X_1+1.11X_2+3.63X_3+5.73X_4, \quad (EQ. 4)$$

where $X_1$ is the percentage of the alite, $X_2$ is the percentage of the belite, $X_3$ is the average grain size of alite expressed in percents and $X_4$ is the average grain size of belite expressed in percents.

The above and other prior art methods are expensive and complicated, and require either transportation of a sample to the laboratory or a highly trained material scientist or technician having the proper instrumentation in the construction site.

Since cement stone, concrete and other similar materials at any stage of hardening are poly-dispersed moist capillary-porous bodies, concrete strength can determined by measuring the energy of physically bound water, which is contained in the pores and capillaries of its structure. This energy is indicative of the porosity of the material and therefore of its strength.

Water (both in a liquid and gaseous form) is always in a state of thermodynamic equilibrium with the porous solid phase with which it interacts. Thus, the properties of water (viscosity, bounding energy, relaxation time, etc.) are changing in strict accordance with structure formation and, consequently, with the strength growth of the hardening material. To this end, see, for example, Shtakelberg D., I., supra; Shtakelberg D. I., "Thermodynamics of water-silicate disperse materials structure-formation," Riga, Zinatne, 1984; and Neville M. "Properties of concrete," Longman Scientific & Technical. NT., 1988.

In a newly compressed cement paste, whose strength is minimal, e.g., in the order of $10^{-1}$ Mpa, practically all the water is distributed between the grains of a non-hydrated cement. The average distance between the grains is approximately 5–10 μm. At this state, the bond energy of water molecules and the material constitutes only a few kDz/mol. While hardening, a portion of the water becomes chemically bound, i.e., transforms into a solid state with bond energy in the order of 1000 kDz/mol. Another portion of the water is contained in the pores of the formed cement gel. The size of these pores is less than $10^{-3}$ μm in diameter and the bond energy in this case is up to 50 kDz/mol. Another portion of the water occupies capillaries of a larger diameter ($10^{-2}$–$10^{-1}$ μm) with bond energy of up to 10–20 kDz/mol.

Information pertaining to the energy level of water contained in a concrete structure reflects its porosity, which, in turn reflects its strength. Therefore, it is possible to obtain a far more reliable correlation between the energy of water contained in a concrete structure and its strength.

It was already noted above that physically-chemically bound water in capillary-porous bodies always coexists in thermodynamic equilibrium with the solid phase. Nevertheless, all quality changes developing in cement stone and concrete during the process of structure forming and hardening, such as, chemical dispergation, colloidation, coagulation, crystallization, nucleation, development of inner cracks, etc., are almost immediately reflected by the energy of the liquid stage thereof. This is why, namely, the physically bound water is the most informative component of capillary-porous structures for quality evaluation of energetic level and consequently strength and other physical-mechanical properties.

There are various of absorption methods for quantitating (in terms of mass) and qualitating (in terms of energy) chemically and physically bound water in capillary-porous bodies. However, these methods are rather complicated and labor-consuming. Moreover, performance of such measurements in areas of a high relative water vapor pressure is complicated due to development of capillary condensation. In addition, adsorption methods are suitable solely for testing the samples of cement stone, concrete, etc., with a completely-formed or artificially stabilized structure.

U.S. Pat. No. 6,396,265, the contents of which are hereby incorporated by reference, discloses a method of prediction a strength of a chemically active material by performing a high frequency, spin-echo nuclear magnetic resonance (NMR) measurement of the water. More specifically, in the NMR method, a first spin echo NMR measurement is performed at the moment of setting-start of the concrete, and a second spin echo NMR measurement is performed at the moment of setting-finish of the concrete. On the basis of these NMR measurements, a relation of RF-field absorption of energy of physically bound water is determined.

Although the NMR method is significantly more efficient than the absorption methods, this method requires an NMR apparatus to be present at the construction cite. It is appreciated that such apparatus is expensive and is primarily designated for the purpose of laboratory studies.

There is thus a widely recognized need for, and it would be highly advantageous to have, a method, apparatus and system for measuring and forecasting strength of chemically active materials while hardening devoid of the above limitations.

SUMMARY OF THE INVENTION

According to one aspect of the present invention there is provided a method of forecasting strength of a chemically active material while hardening, the chemically active material being characterized by at least one physical parameter, the method comprising: (a) measuring the at least one physical parameter over a predetermined time-interval, so as to obtain at least one series of measurements; (b) extracting a predetermined time-dependence of the at least one physical parameter over at least a portion of the predetermined time-interval; and (c) using the predetermined time-dependence of the at least one physical parameter to forecast the strength of the chemically active material at a future time.

According to another aspect of the present invention there is provided a method of forecasting strength of a chemically active material while hardening, the method comprising: (a) selecting at least one physical parameter characterizing the chemically active material; (b) measuring the at least one physical parameter over a predetermined time-interval, so as to obtain at least one series of measurements; (c) extracting a predetermined time-dependence of the at least one physical parameter over at least a portion of the predetermined time-interval; and (d) using the predetermined time-dependence of the at least one physical parameter to forecast the strength of the chemically active material at a future time.

According to yet another aspect of the present invention there is provided a method of forecasting strength of a structure made of concrete while hardening, the method comprising: (a) measuring at least one physical parameter characterizing the concrete over a predetermined time-interval, so as to obtain at least one series of measurements; (b) extracting a predetermined time-dependence of the at least one physical parameter over at least a portion of the predetermined time-interval; and (c) using the predetermined time-dependence of the at least one physical parameter to forecast the strength of the concrete at a future time.

According to further features of preferred embodiments of the invention described below, the at least one physical parameter is selected from the group consisting of energy, density, sound wave velocity, electrical conductivity, electrical resistance, electrical capacitance, dielectric permittivity, heat capacity, viscosity, shear stress, plastic strength, shrinkage and any combination thereof.

According to still further features in the described preferred embodiments the step of forecasting the strength of the chemically active material at the future time comprises: (i) extracting a representative quantity of the predetermined time-dependence; and (ii) expressing the strength of the chemically active material at the future time in terms of the representative quantity, using a predetermined forecasting function.

According to still further features in the described preferred embodiments at least one of the steps of the methods is performed in situ.

According to still further features in the described preferred embodiments the step of forecasting the strength of the concrete at the future time comprises: (i) extracting a representative quantity of the predetermined time-dependence; and (ii) expressing the strength of the concrete at the future time in terms of the representative quantity, using a predetermined forecasting function.

According to still another aspect of the present invention there is provided an apparatus for forecasting strength of a chemically active material while hardening, the chemically active material being characterized by at least one physical parameter, the apparatus comprising: (a) an input unit for inputting at least one series of measurements of the at least one physical parameter over a predetermined time-interval; (b) an extractor for extracting a predetermined time-dependence of the at least one physical parameter over at least a portion of the predetermined time-interval; and (c) a forecasting unit for forecasting the strength of the chemically active material at a future time, using the predetermined time-dependence of the at least one physical parameter.

According to an additional aspect of the present invention there is provided a system for forecasting strength of a chemically active material while hardening, the chemically active material being characterized by at least one physical parameter, the system comprising: (a) a measuring device for measuring the at least one physical parameter over a predetermined time-interval, so as to obtain at least one series of measurements; (b) an input unit for inputting the at least one series of measurements; (c) an extractor for extracting a predetermined time-dependence of the at least one physical parameter over at least a portion of the predetermined time-interval; and (d) a forecasting unit for forecasting the strength of the chemically active material at a future time, using the predetermined time-dependence of the at least one physical parameter.

According to further features of preferred embodiments of the invention described below, the measuring device is selected from the group consisting of a nuclear magnetic resonance device, an acoustical device, a rheology device, an electrical device, a thermal device and any combination thereof.

According to still further features in the described preferred embodiments an overlap between the predetermined time-interval and a setting time-interval is from about 90 percents to about 110 percents, the setting time-interval being defined between a setting-start point of the chemically active material and a setting-finish point of the chemically active material.

According to still further features in the described preferred embodiments the predetermined time-dependence comprises a monotonic function.

According to still further features in the described preferred embodiments the monotonic function comprises a power-law function.

According to still further features in the described preferred embodiments the monotonic function has a linearity of more than about 90 percents.

According to still further features in the described preferred embodiments the monotonic function has a linearity of more than about 93 percents.

According to still further features in the described preferred embodiments the monotonic function has a linearity of more than about 95 percents.

According to still further features in the described preferred embodiments the forecasting unit comprises: (i) a first electronic-calculation functionality for extracting a representative quantity of the predetermined time-dependence; and (ii) a second electronic-calculation functionality for expressing the strength of the chemically active material at the future time in terms of the representative quantity, using a predetermined forecasting function.

According to still further features in the described preferred embodiments the predetermined forecasting function is monotonic.

According to still further features in the described preferred embodiments the predetermined forecasting function comprises a power-law function.

According to still further features in the described preferred embodiments the power-law function is characterized by an exponent ranging from about 0.9 to about 1.1.

According to still further features in the described preferred embodiments the predetermined forecasting function is substantially linear.

According to still further features in the described preferred embodiments the representative quantity is dimensionless.

According to still further features in the described preferred embodiments the representative quantity equals a derivative of the predetermined time-dependence.

According to still further features in the described preferred embodiments the derivative is selected from the group consisting of a first derivative and a second derivative.

According to still further features in the described preferred embodiments the representative quantity equals a difference between two values of the at least one physical parameter.

According to still further features in the described preferred embodiments the representative quantity is a ratio between a first value of the at least one physical parameter and a second value of the at least one physical parameter, the first and the second values of the at least one physical parameter being measured at two different time points within the at least the portion of the predetermined time-interval.

According to still further features in the described preferred embodiments the representative quantity is a value of the monotonic function or a combination of a plurality of values of the monotonic function.

The present invention successfully addresses the shortcomings of the presently known configurations by providing a method, apparatus and system for forecasting strength of chemically active materials, enjoying properties far exceeding prior art technologies.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
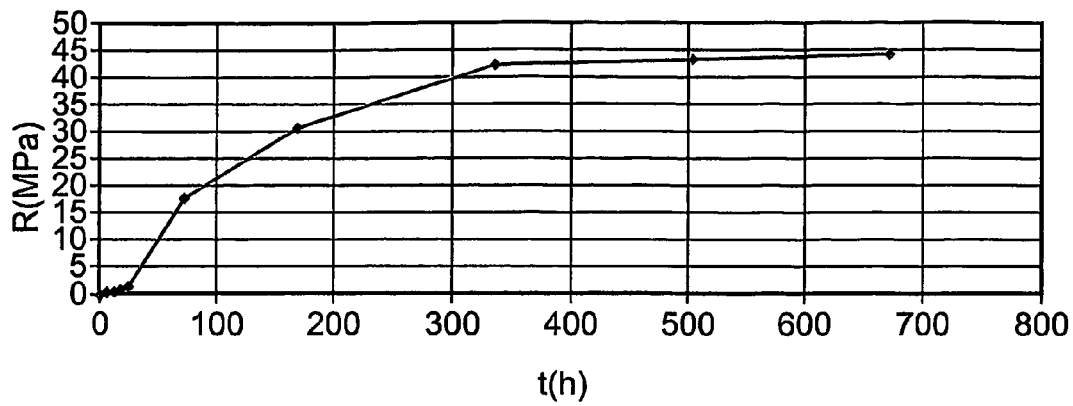
FIGS. 1a–b show typical strength curves of a cement of type CEM-1 Portland (42.5N), according to the European Standard EN-197.
Figure 1B:
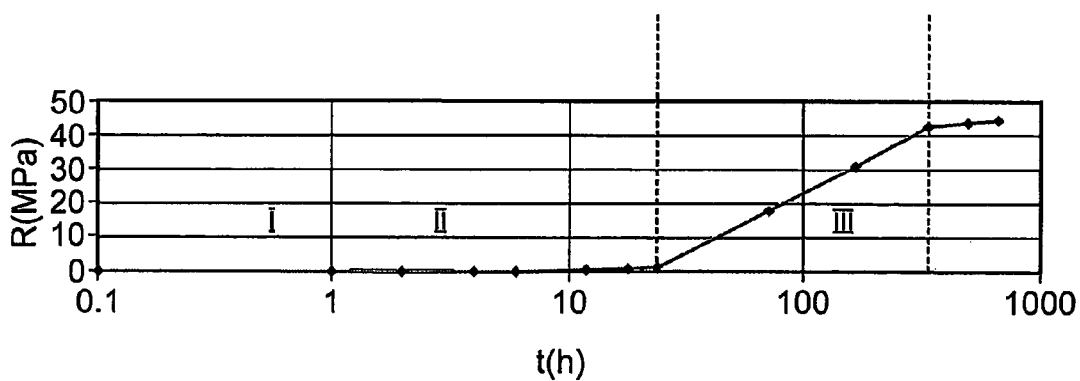

The present invention is of a method, apparatus and system for measuring and forecasting strength of chemically active materials while hardening, which can be used for forecasting strength of various compositions and structures. Specifically, the present invention can be used to forecast strength of a structure made of a cementations material, such as, but not limited to, concrete.

The principles and operation of a method, apparatus and system for measuring and forecasting strength according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As stated in the Background section above, while hardening, a chemically active material generally experiences transitions between three states: (i) continues liquid phase and discrete solid phase; (ii) discrete liquid phase and discrete solid phase; and (iii) discrete liquid phase and continues solid phase.

Hardening and strengthening of chemically-active materials ensue from a joint development of complex physical and chemical processes. The motivating force of these processes is the chemical reaction of hydration as well as the hydrolyzation of the mineral binders (cement, gypsum, lime, etc.) present in the material. As soon as a sufficient amount of product resulting from these reactions is accumulated per volume unit, a capillary-porous structure begins to form, first as a coagulation structure (long-range and short-range), and thereafter as colloidal and crystallization structures of states (ii) and (iii).

It is recognized that the final strength of the material is determined already at the early stages of the hardening process. While at the beginning of the formation of the first state the properties acquired by the material are reversible, once short-range coagulation structure is formed, the properties of the material become irreversible.

The reason of the reversibility at the beginning of the formation of the first state is the long-range coagulation structure of the material. This structure features thixotropic properties which allow for reverse processes, e.g., under application of certain mechanical action, to occur. On the other hand, in the short-range coagulation structure, the formation of the initial crystalline frame finalizes all mechanical transitions within the material hence preventing reverse processes from occurring.

Thus, the crystallization strengthening process deterministically evolves from the initial conditions set at the time of short-range coagulation structure formation. As these initial conditions depend on the mechanical state of the material when its structure still has a long-range nature, it is appreciated that mechanical transitions occurring at that time substantially determine the subsequent crystallization of the material, hence also its strength.

While conceiving the present invention it has been hypothesized and while reducing the present invention to practice it has been realized that the first state of the chemically active material carries sufficient amount of information regarding the strength thereof at a future time. It has been found by the present Inventor that this information can be retrieved from any physical parameter characterizing the material at the time the material is in its first state of hardening, provided a proper analysis method is employed.

Thus, according to one aspect of the present invention there is provided a method of forecasting strength of a chemically active material while hardening. The embodiments and examples of the present invention are described herein mostly with reference to the curing of concrete. However, it is appreciated that the present invention is applicable not only to curing of concrete, but to any chemically active material which contains a liquid which undergoes metamorphosis during hardening, and in which a measurement may be made of at least one stages of the material while hardening.

Figure 2:
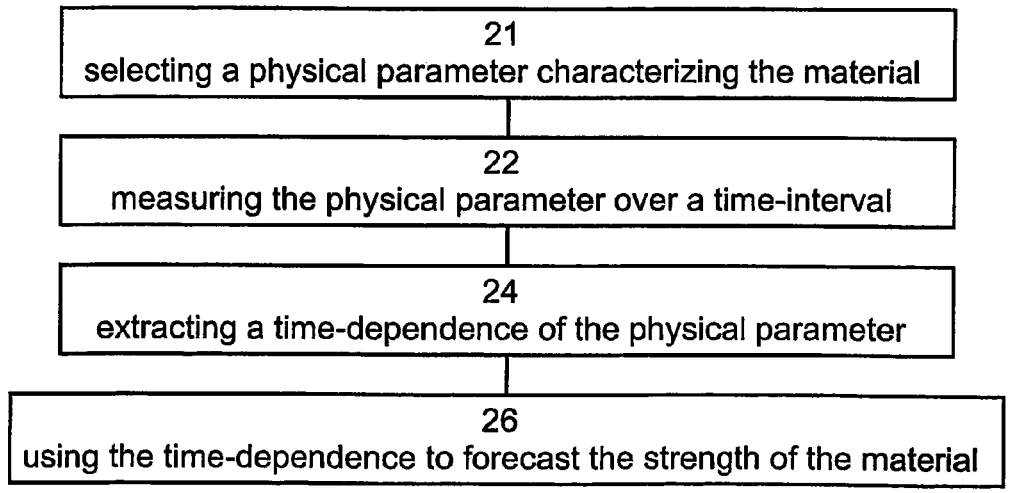
FIG. 2 is a flowchart diagram of a method of forecasting strength of a chemically active material while hardening, according to a preferred embodiment of the present invention.

Referring now to the drawings, the method comprises the following method steps which are illustrated in the flowchart of FIG. 2. In a first step of the method, designated in FIG. 2 by Block 22, at least one physical parameter characterizing the material is measured over a predetermined time-interval.

The predetermined time-interval is preferably selected such that a sufficient amount of information is collected in the first step of the method. This time-interval typically depends on the material (its original chemical structure, certain additives mixed therewith, etc.) and/or on external conditions (temperature, humidity, etc.). It is well known that a chemically active material is typically characterized by a setting time-interval, defined as the interval between a setting-start point and a setting-finish point of the material (see, e.g., ASTM C-191 "Standard Test Method for Time of Setting of hydraulic cement by Vicat Needle").

Thus, according to a preferred embodiment of the present invention the predetermined time-interval and the setting time-interval have a certain degree of mutual overlap. For example, the predetermined time-interval during which the measurement of the physical parameter is performed may be from one or more hours before the setting-start point to one or more hours after the setting-finish point. Alternatively, the predetermined time-interval may be from approximately the setting-start point to one or more hours after the setting-finish point. Still alternatively, the predetermined time-interval may be from approximately the setting-start point or after to approximately the setting-finish point or before.

Generally, denoting the setting-start point by $t_s$ and the setting-finish point by $t_f$, the predetermined time interval is preferably from $xt_s$ to $yt_f$, where x and y are dimensionless parameters, each independently ranging from about 0.9 to about 1.1 so that the overlap between the predetermined time-interval and the setting time-interval is from about 90% to about 110%.

As used herein the term "about" refers to ±10%.

A particular feature of the present embodiments of the invention is that any physical parameter characterizing the material at the time step 22 is performed, can be selected and measured, depending on the method which is used to perform this measurement. Following are several examples for such methods which are not to be considered as limiting.

Hence, in one embodiment the measurement is performed by acoustic means, such as, but not limited to, resonance technique, ultrasound pulses or acoustic emission. In this embodiment the physical parameter can be, for example, a velocity of a sound wave. Methods and apparati for acoustic measurements of chemically active materials are known in the art and can be found, for example, in Jones R., "Non-destructive testing of concrete," Cambridge University Press, 1962; Jones R. and Facaoaru I., "Non-destructive test methods of concrete," Editura technica, Bucharest, 1968; Dzenis V., "Application of ultra-sonic transducers with point contact for non-destructive testing," Zinantne Publishing House, Riga, 1987; Kakuta S. and Kojima T., "Evaluation of very early age concrete using wave propagation method. Quality control of concrete structures," Proceedings of the International Symposium by RILEM, E&FN Spon, Ghent, 1991, pp. 163–172; Muravin G., "Determination of concrete behavior in structures on the basis of acoustic emission data," Progress in Acoustic Emission, Sendai, V, 1990, pp. 337–344; Nielsen J. and Griffin D., "Acoustic emission of plain concrete," Journal of Testing and Evolution, USA, v. 5, No. 6, 1977, pp. 476–483.

In another embodiment, the measurement of step 22 is performed by electrical means, in which case the physical parameter can be any electrical quantity, such as, but not limited to, electrical conductivity, electrical resistance, electrical capacitance or dielectric permittivity. Methods and apparati for electrical measurements of chemically active materials are known in the art and can be found, for example, in Achverdow I., "Basis of physics of concrete," Stroyizdat Press, Moscow, 1981; McCarter W., Forde M. and Whittington H., "Resistivity characteristics of concrete," Proc. ICE, Pt. 2, No. 71, 1981, pp. 107–118; Van Beek A., Van Breugel K. and Hilhorst M., "Monitoring system for hardening concrete based on dielectric properties," Dundee: Creating with concrete. Utilizing of ready-mixed concrete and mortar, 1999, pp. 303–312.

In an additional embodiment, the measurement of step 22 is performed by rheologic means, in which case the physical parameter can be any rheology related quatity, such as, but not limited to, viscosity, shear stress and plastic resistance. Methods and apparati for theological measurements of chemically active materials are known in the art and can be found, for example, in Rebinder P. A. and Segalova E. E., "Beginning of crystallization structures and conditions of strength development," New in Chemistry and Technology of Cement, Moscow, "Gosstroyizdat" Press, 1962, pp. 202–215; Kunnos G. et al., "Die Steuerungsgrundlagen der Herstellungstechnologie von Zellenbetonen auf der Gasbildnerbasis," 2. Internationales Symposium für dampfgehärtetes Kalziumsilikat. Baustoffe, 92, Hanover, 1969, s. 16.

In still another embodiment, the measurement of step 22 is performed by calorimetric means, in which case the physical parameter can be any thermal quantity, such as, but not limited to, heat capacity. Methods and apparati for calorimetric measurements of chemically active materials are known in the art and can be found, for example, in Legrand C. and Wirquin E., "Influence of initial microstructuring in the interfacial transition zone on early hydration-strength binding," RILEM 2-nd International Conference on: The ITZ in Cementitious Composites, Haifa, 1998, pp. 275–281.

In yet another embodiment, the measurement of step 22 is performed by nuclear magnetic resonance (NMR), in which the physical parameter can be a relaxation time distribution. This distribution is related to the energy of bound water present in the material, hence also to the fraction of this water in the material. Methods and apparati for NMR measurements of chemically active materials can be found, for example, in U.S. Pat. No. 6,396,265.

Additionally, any combination of the above and other physical parameters can be employed, provided the selected physical parameter(s) or the combination thereof characterizes the material. More specifically, one or more of the aforementioned methods or other can be used, so that more than one quantity is measured, in which case the physical parameter is preferably defined as a combination between the measured quantities. For example, a combination of several thermal related quantities (e.g., a ratio of heat capacity at constant pressure to heat capacity at constant volume) can be used.

According to a preferred embodiment of the present invention the measurement of the physical parameter(s) is made in situ and the forecasting of the strength is performed essentially in real time, so as to provide reliable and quick information to the builder and virtually eliminating any financial risk. As further detailed hereinunder and in the Example section that follows, preferred embodiments of the present invention provide a simple and efficient procedure for performing the data analysis which follows the measuring step. For example, in the case of concrete curing, the analysis can be made within a few hours instead of the 28 days of the prior art. It is to be understood that it is not intended to limit the scope of the present invention to in situ measurement, and other locations are not excluded. For example, as the concrete's strength is predicted already at the early stages of hardening, a sample of the concrete can be taken to a laboratory where the measurement and/or data analysis can take place.

For each physical parameter which is measured, a series of measurements is preferably obtained. For the purpose of simplifying the description, in what follows, a single measured physical parameter is assumed. It is to be understood that the following description can be extended to any number of physical parameters, and any such number is within the scope of the present invention. The physical parameter(s) may be selected prior to the execution of step 22 of the method (this selection is designated by Block 21 in FIG. 2).

In a second step of the method, designated 24, a predetermined time-dependence of the physical parameter is extracted from the series of measurements. This predetermined time-dependence corresponds to at least a portion of the series hence to a portion of the predetermined time-interval.

According to a preferred embodiment of the present invention the extracted time-dependence comprises a monotonic function, such as, but not limited to, a power-law function. More specifically, the time-dependence preferably has a form $k\, t^\lambda + h$, where k, h and $\lambda$ are constants. Preferably, $\lambda$ is selected to have a value close to unity (e.g., from about 0.9 to about 1.1). The values of k and h are not limited. These are free parameters which are extracted from the series of measurements. One ordinarily skilled in the art would appreciate that when $\lambda=1$, the time-dependence of the physical parameter is linear. On the other hand, it is appreciated that the dataset is not synthetic and some variations may occur, e.g., due to systematic or statistical errors in the measurements. Thus, according to a preferred embodiment of the present invention the monotonic function has a certain degree of linearity, which is determined by the dominance of a first derivative over higher orders derivatives of the function. The minimal linearity of the function, according to a preferred embodiment of the present invention, is about 90%, more preferably about 93%, most preferably about 95%.

As demonstrated in the Example section that follows, when a linear time-dependence is selected, the slope of the linear function (the parameter k above) is substantially universal for many different physical parameters. In other words, a change in the measured quantity leaves the shape of the linear function invariant within reasonable limits (say, ±10%). Thus, irrespectively of the device which is employed to perform the measurements of step 22, a universal function can be extracted from a portion of the series, which universal function represents the time-dependence of the physical parameter over a portion of the predetermined time-interval.

In a third step of the method, designated by Block 26 the time-dependence is used for forecasting the strength of the chemically active material at a future time. This can be done, for example, by extracting a representative quantity, $\Pi$, of the time-dependence (e.g., a value of the monotonic function or a combination of values thereof) and expressing the strength of the material in terms of $\Pi$. In one embodiment, $\Pi$ is dimensionless and can be, for example, a ratio between two values of the physical parameter measured at two different time points. Specifically, denoting the value of the physical parameter by p, the representative quantity, $\Pi$, preferably equals $p_2/p_1$, where $p_2$ and $p_1$ denote two different values of p, measured at two different times, $t_2$ and $t_1$, respectively, over the time-interval in which the extracted time-dependence is applicable. Alternatively, instead of using measured values, $p_2$ and $p_1$ can be calculated directly from the extracted time-dependence.

In another embodiment, $\Pi$ equals a certain derivative of the extracted time-dependence, for example, a first derivative, whereby $\Pi$ represents a local or global slope of time-dependence, a second derivative, whereby $\Pi$ represents a local or global curvature of the time-dependence, and the like.

In an additional embodiment, $\Pi$ equals a difference between two different values of the physical parameter.

One of ordinary skill in the art would appreciate that although for different physical parameters may have different values, a ratio as defined hereinabove can be a substantially invariant quantity.

Once $\Pi$ extracted, the strength of the chemically active material at a future time is preferably expressed using a forecasting function, in which $\Pi$ its argument. According to a preferred embodiment of the present invention the forecasting function is monotonic, e.g., a power-law function or a substantially linear function as further detailed hereinabove.

For example, when a linear function is employed, the strength of the material can be calculated using the following equation:

$$R_n = a\Pi + b, \qquad (EQ. 5)$$

where a and b are constant parameters and n is the time at which the strength of the material is to be calculated. For standard cement-sand mortar according to European standard EN-196, Part. 1, n is typically about 28 days a is typically from about 26.0 to about 28.0 and b is typically from about 8.0 to about 11.5.

Figure 3:
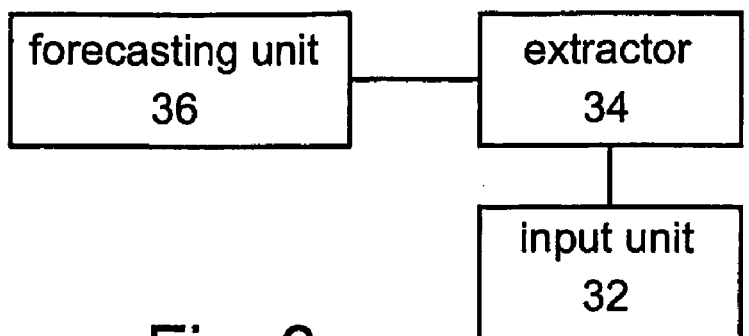
FIG. 3 is a schematic illustration of an apparatus for forecasting strength of a chemically active material while hardening, according to a preferred embodiment of the present invention.

FIG. 3 illustrate several embodiments of an apparatus according to another aspect of the present invention, which is generally referred to hereinbelow as apparatus 30. Apparatus 30 can be used to effect the methods according to preferred embodiments of the present invention, hence to forecast strength of chemically active materials.

Referring to FIG. 3, in its simplest configuration apparatus 30 comprises an input unit 32, an extractor 34 and a forecasting unit 36. Input unit 32 serves for inputting the values of the physical parameter, which, as stated are preferably measured over a predetermined time-interval. Extractor 34 serves for extracting the time-dependence of the physical parameter, which is preferably embodied as a monotonic function as further detailed hereinabove. Forecasting unit 36 receives the time-dependence from extractor 34 and forecast the strength of the material at a future time. According to a preferred embodiment of the present invention unit 36 first extracts Π and thereafter using a monotonic function to express the strength of the material in terms of Π (see, e.g., Equation 5).

According to an additional aspect of the present invention there is provided a system 40 for forecasting strength of chemically active material 42.

Figure 4:
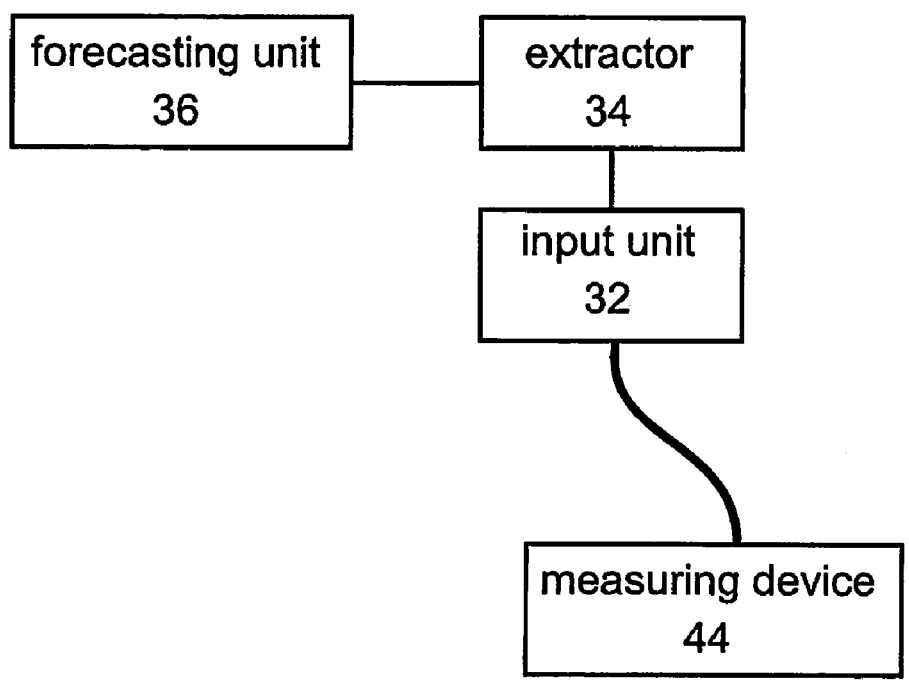
FIG. 4 is a schematic illustration of a system for forecasting strength of a chemically active material while hardening, which includes the elements of the apparatus of FIG. 3 and a measuring device, according to a preferred embodiment of the present invention.
Figure 4:

FIG. 4 is a schematic illustration of system 40 which, beside input unit 32, extractor 34 and forecasting unit 36 (see apparatus 30 above), preferably comprises a measuring device 44 for measuring the physical parameter of material 42 over the aforementioned time-interval. Measuring device 44 communicates with input unit 32 (e.g., electrically, thermally, mechanically) and can be any known device capable of measuring the physical parameter of material 42, and transmitting the information to unit 32. More specifically, device 44 preferably capable of measuring energy, density, sound wave velocity, electrical conductivity, electrical resistance, electrical capacitance, dielectric permittivity, heat capacity, viscosity, shear stress, plastic strength, shrinkage and the like. Thus device 44 may comprise, for example, an NMR device, an acoustical device, a rheology device, an electrical device, a thermal device or any combination thereof. Other measuring devices are not excluded from the present invention.

It is expected that during the life of this patent many relevant methods and devices for measuring physical parameters of a chemically active material will be developed and the scope of the term measuring device is intended to include all such new technologies a priori.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE

Reference is now made to the following example, which, together with the above descriptions, illustrates the invention in a non limiting fashion.

Measurements were performed on different samples of cement, according to a preferred embodiment of the present invention. The following measurements were continuously taken from before setting-start point to after setting finish points of the samples.

NMR Measurements A high frequency spin-echo NMR method was used to measure the distribution on physically bound water in a sample of standard cement-sand mortar (C:S=1:3, C/W=0.5 according to European Standard EN-196, Part 1).

The distribution of the water was measured according to energy levels, which are characterized by corresponding values of $T_2$ relaxation times. There is a known (linear) relation between the amount of physically bound water in a concrete structure and the amplitude of NMR measurement generated by this water. In addition, the energy, which is delivered from the radiofrequency electromagnetic field to the physically bound water, depends on the $T_2$ relaxation time [A. Abraham, "Principles of Nuclear Magnetism," Oxford, Clarendon Press, 1996]. Thus, application of a NMR spin-echo pulse sequence allows for a determination of the energy of the physically bound water.

Figure 5:
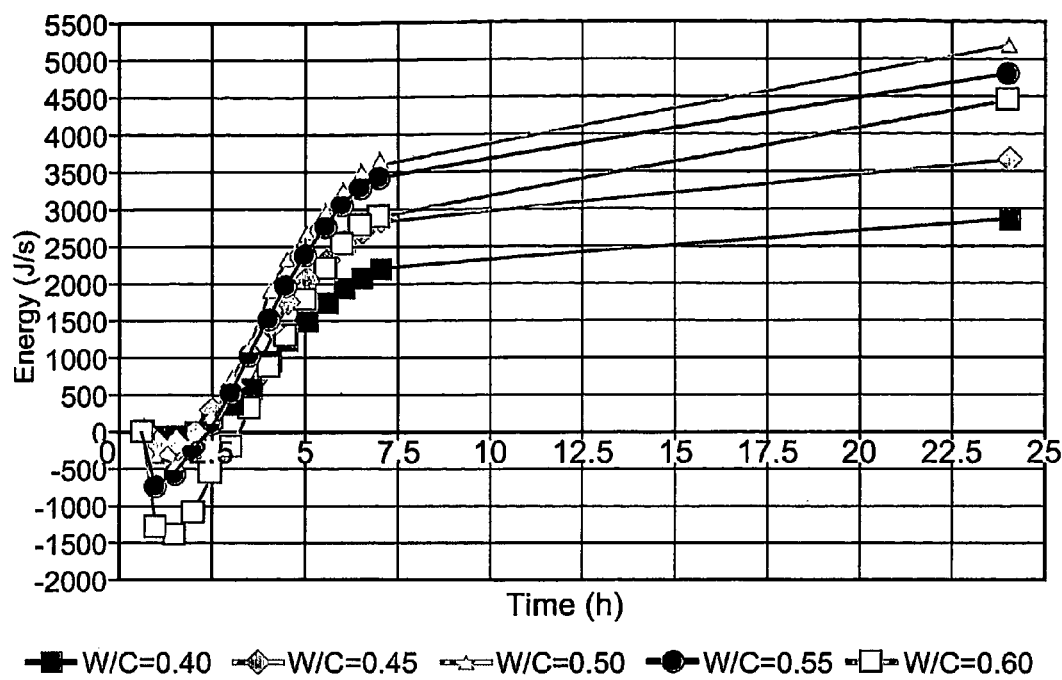
FIG. 5 shows the energy per unit time of physically bound water, in units of J/s, as a function of time, according to a preferred embodiment of the present invention.

FIG. 5 shows the energy per unit time of physically bound water, in units of J/s, as a function of time for five different water/cement ratios: 0.40, 0.45, 0.50, 0.55 and 0.60. As shown in FIG. 5, all curves exhibits similar time-dependence at the time-interval of approximately 7.5–23 hours.

Acoustic Measurements

A sample of standard cement-sand mortar was irradiated by ultrasonic waves using an ultrasound device.

It is recognized that the hardening stage of the material can be determined by ultrasonic radiation [Jones R. ibid]. In this experiment, the physical parameter which was selected is the velocity of the sound wave within the sample. As the propagation of the (longitudinal) acoustic wave through any material essentially depends on its internal structure (density, crystallization axes, etc.) the measurement of the sound wave velocity provides sufficient information on the structure of the sample at the time the measurement is made.

Figure 6A:
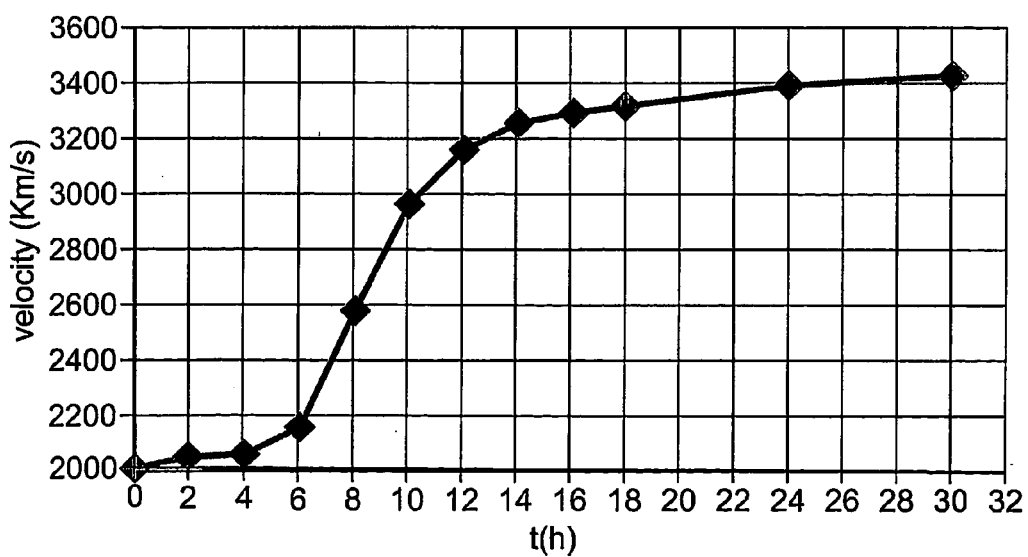
FIGS. 6a–b show sound wave velocity in units of Km/s (FIG. 6a) and m/s (FIG. 6b) as a function of time, according to a preferred embodiment of the present invention.
Figure 6B:
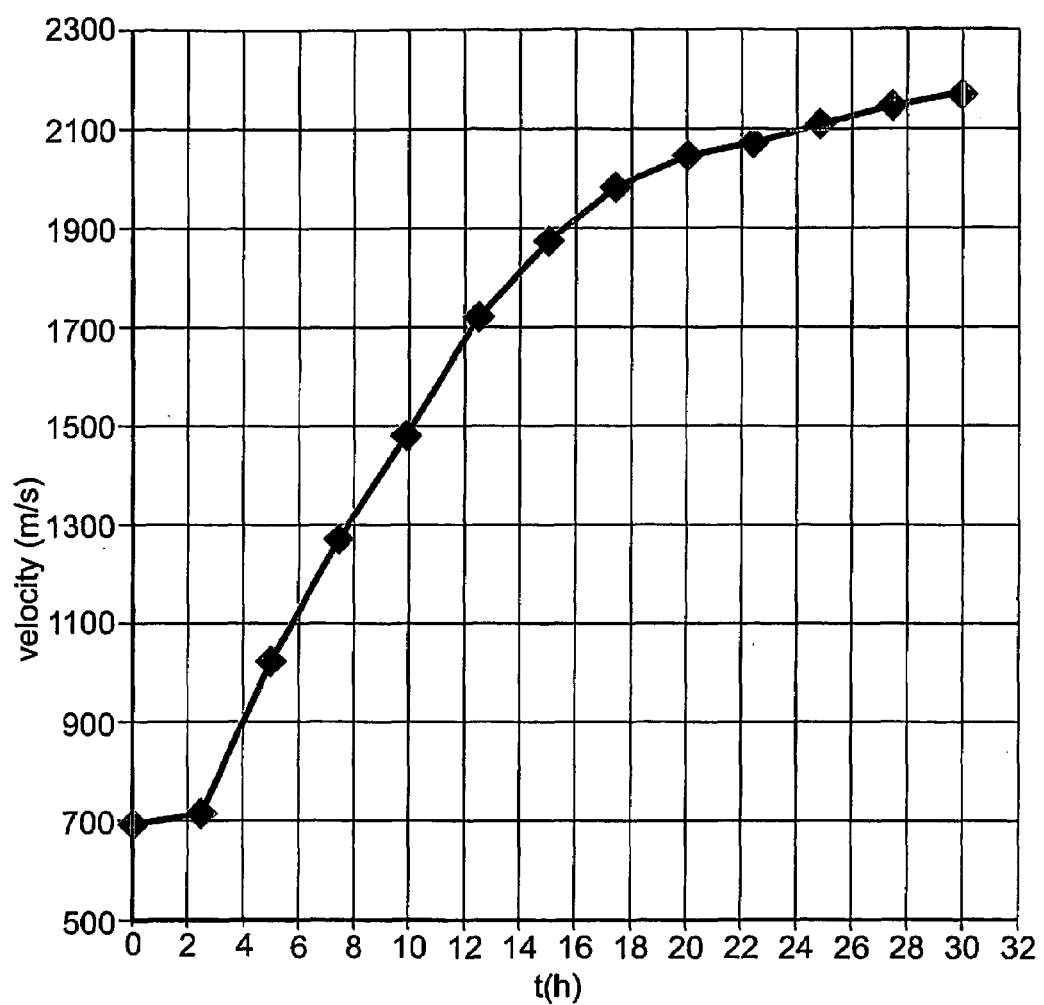

FIGS. 6a–b, show two results of the aforementioned acoustic measurements.

FIG. 6a shows the sound wave velocity in units of Km/s as a function of time for rapid hardened cement (see Jones R. and Facaoaru I., supra); and FIG. 6b shows the sound wave velocity in units of m/s as a function of time for asbestos-cement (see Dzenis V., supra)

Calorimetric Measurements

A sample of cement-limestone mortar with W/C=0.45 was tested using a semi-adiabatic colorimetr (see Legrand C. and Wirquin E., supra).

The physical parameter which was selected in this example is the amount of heat developed on the sample. This parameter is known to reflect the microstructure of the concrete, especially in the interfacial transition zone at early hydration-strength binding.

Figure 7:
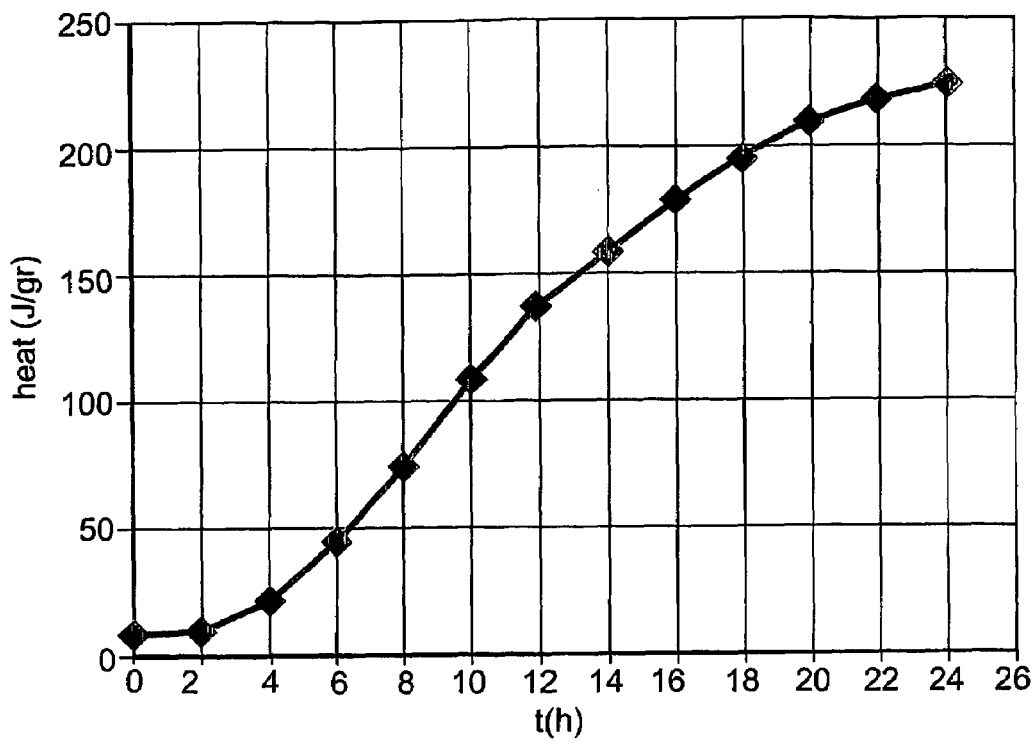
FIG. 7 shows amount of heat per unit mass, in units of J/gr, developed on a concrete sample, as a function of time, according to a preferred embodiment of the present invention.

FIG. 7 shows the amount of heat per unit mass, in units of J/gr, developed on the sample, as a function of time.

Electrical Measurements

The electrical conductivity of a sample of a B-30 concrete was measured using a conductivity meter.

The electrical resistance, and many other electrical observables, such as, but not limited to, conductivity, capacitance, dielectric permittivity, are known to depend on the internal structure as well as on the amount of liquid present in the concrete.

Figure 8:
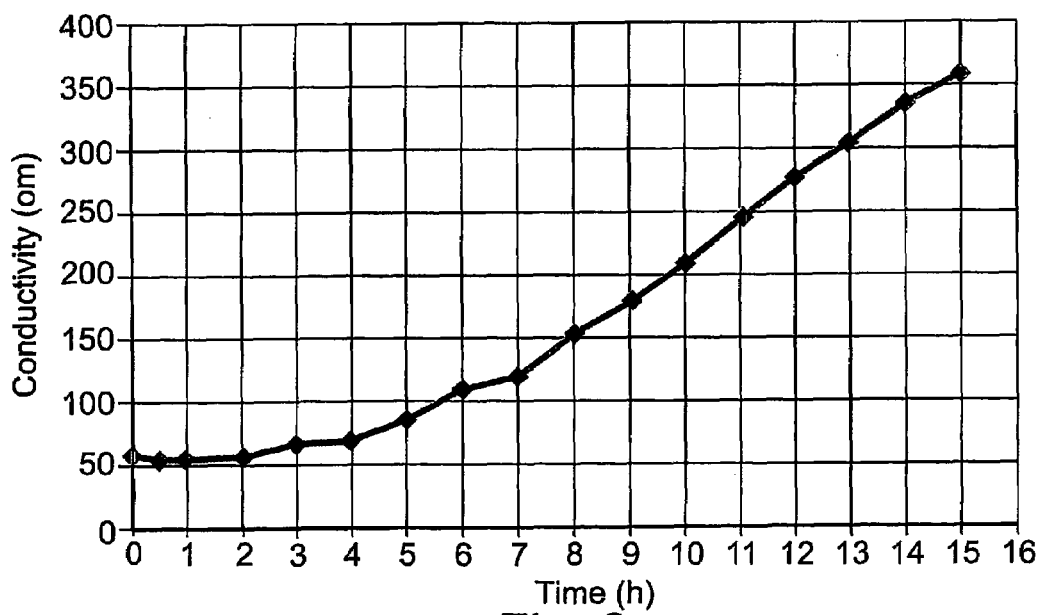
FIG. 8 shows electrical resistance of a concrete sample, measured in units of Ohms, developed on as a function of time, according to a preferred embodiment of the present invention.

FIG. 8 shows changes of electric conductivity of the sample as a function of time.

Universality

Figure 9:
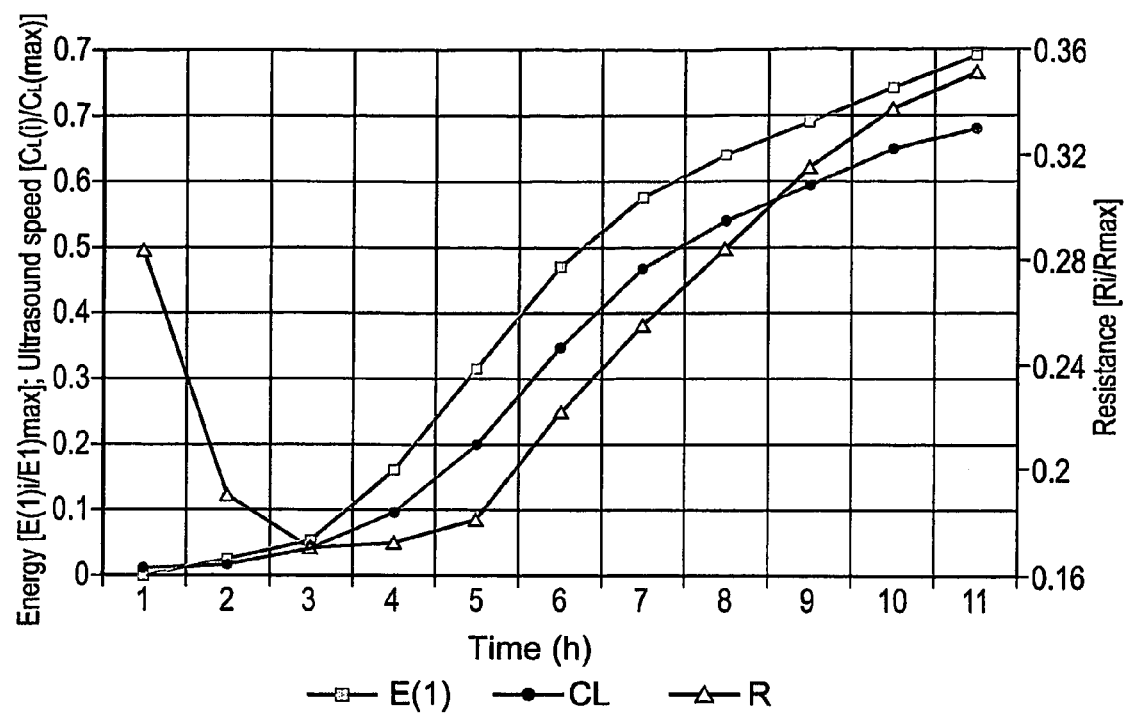
FIG. 9 shows similarities between the linear portions of different physical parameters, according to a preferred embodiment of the present invention.

Similarities between the linear portions of different physical parameters are shown in FIG. 9. Specifically, FIG. 9 shows the energy (squares), sound wave velocity (circles) and electrical resistance (triangles) as a function of time. As shown on the figure, the linear portion of all curves is substantially parallel. Thus, irrespectively of the physical parameter which is selected, a universal time-dependence can be extracted at the early stages of the hardening process, from which the strength of the cement-sand mortar (C:S=1:3, C/W=0.5, according to European Standard EN-196, Part 1) can be forecasted at a future time.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of forecasting strength of a chemically active material while hardening, the chemically active material being characterized by at least one physical parameter, the method comprising:
   (a) measuring the at least one physical parameter over a predetermined time-interval, so as to obtain at least one series of measurements, said measurements being selected from the group consisting of NMR measurements, acoustic measurements, calorimetric measurements and electrical measurements;
   (b) extracting a predetermined monotonic time-dependence of the at least one physical parameter over at least a portion of said predetermined time-interval, said predetermined monotonic time-dependence comprising a power-law function; and
   (c) using said predetermined time-dependence of the at least one physical parameter to forecast the strength of the chemically active material at a future time.

2. The method of claim 1, wherein the at least one physical parameter is selected from the group consisting of energy, density, sound wave velocity, electrical conductivity, electrical resistance, electrical capacitance, dielectric permittivity, heat capacity, viscosity, shear stress, plastic strength, shrinkage and any combination thereof.

3. The method of claim 1, wherein an overlap between said predetermined time-interval and a setting time-interval is from about 90 percents to about 110 percents of said setting time-interval, said setting time-interval being defined between a setting-start point of the chemically active material and a setting-finish point of the chemically active material.

4. The method of claim 1, wherein said power-law function is characterized by an exponent ranging from about 0.9 to about 1.1.

5. The method of claim 1, wherein said monotonic function has a linearity of more than about 90 percents.

6. The method of claim 1, wherein said monotonic function has a linearity of more than about 93 percents.

7. The method of claim 1, wherein said monotonic function has a linearity of more than about 95 percents.

8. The method of claim 1, wherein said step of forecasting the strength of the chemically active material at said future time comprises:
   (i) extracting a representative quantity of said predetermined time-dependence; and
   (ii) expressing the strength of the chemically active material at said future time in terms of said representative quantity, using a predetermined forecasting function.

9. The method of claim 8, wherein said predetermined forecasting function is monotonic.

10. The method of claim 9, wherein said predetermined forecasting function comprises a power-law function.

11. The method of claim 10, wherein said power-law function is characterized by an exponent ranging from about 0.9 to about 1.1.

12. The method of claim 9, wherein said predetermined forecasting function is substantially linear.

13. The method of claim 8, wherein said representative quantity is dimensionless.

14. The method of claim 8, wherein said representative quantity equals a derivative of said predetermined time-dependence.

15. The method of claim 14, wherein said derivative is selected from the group consisting of a first derivative and a second derivative.

16. The method of claim 8, wherein said representative quantity equals a difference between two values of said at least one physical parameter.

17. The method of claim 13, wherein said representative quantity is a ratio between a first value of the at least one physical parameter and a second value of said at least one physical parameter, said first and said second values of the at least one physical parameter being measured at two different time points within said at least said portion of said predetermined time-interval.

18. The method of claim 8, wherein said representative quantity is a value of said monotonic function or a combination of a plurality of values of said monotonic function.

19. A method of forecasting strength of a chemically active material while hardening, the method comprising:
   (a) selecting at least one physical parameter characterizing the chemically active material;
   (b) measuring said at least one physical parameter over a predetermined time-interval, so as to obtain at least one series of measurements;
   (c) extracting a predetermined monotonic time-dependence of said at least one physical parameter over at least a portion of said predetermined time-interval, said predetermined monotonic time-dependence comprising a power-law function; and (d) using said predetermined time-dependence of said at least one physical parameter to forecast the strength of the chemically active material at a future time.

20. The method of claim 19, wherein said at least one physical parameter is selected from the group consisting of energy, density, sound wave velocity, electrical conductivity, electrical resistance, electrical capacitance, dielectric permittivity, heat capacity, viscosity, shear stress, plastic strength, shrinkage and any combination thereof.

21. The method of claim 19, wherein an overlap between said predetermined time-interval and a setting time-interval is from about 90 percents to about 110 percents of said setting time-interval, said setting time-interval being defined between a setting-start point of the chemically active material and a setting-finish point of the chemically active material.

22. The method of claim 19, wherein said power-law function is characterized by an exponent ranging from about 0.9 to about 1.1.

23. The method of claim 19, wherein said monotonic function has a linearity of more than about 90 percents.

24. The method of claim 19, wherein said monotonic function has a linearity of more than about 93 percents.

25. The method of claim 19, wherein said monotonic function has a linearity of more than about 95 percents.

26. The method of claim 19, wherein said step of forecasting the strength of the chemically active material at said future time comprises:

(i) extracting a representative quantity of said predetermined time-dependence; and (ii) expressing the strength of the chemically active material at said future time in terms of said representative quantity, using a predetermined forecasting function.

27. The method of claim 26, wherein said predetermined forecasting function is monotonic.

28. A method of forecasting strength of a chemically active material while hardening, the method comprising:

(a) selecting at least one physical parameter characterizing the chemically active material;

(b) measuring said at least one physical parameter over a predetermined time-interval, so as to obtain at least one series of measurements;

(c) extracting a predetermined monotonic time-dependence of said at least one physical parameter over at least a portion of said predetermined time-interval, said predetermined monotonic time-dependence comprising a power-law function; and (d) using said predetermined time-dependence of said at least one physical parameter to forecast the strength of the chemically active material at a future time, by:

(i) extracting a representative quantity of said predetermined time-dependence; and (ii) expressing the strength of the chemically active material at said future time in terms of said representative quantity, using a predetermined monotonic forecasting function which comprises a power-law function.

29. The method of claim 28, wherein said power-law function is characterized by an exponent ranging from about 0.9 to about 1.1.

30. The method of claim 27, wherein said predetermined forecasting function is substantially linear.

31. The method of claim 26, wherein said representative quantity is dimensionless.

32. The method of claim 26, wherein said representative quantity equals a derivative of said predetermined time-dependence.

33. The method of claim 32, wherein said derivative is selected from the group consisting of a first derivative and a second derivative.

34. The method of claim 26, wherein said representative quantity equals a difference between two values of said at least one physical parameter.

35. The method of claim 31, wherein said representative quantity is a ratio between a first value of said at least one physical parameter and a second value of said at least one physical parameter, said first and said second values of said at least one physical parameter being measured at two different time points within said at least said portion of said predetermined time-interval.

36. The method of claim 26, wherein said representative quantity is a value of said monotonic function or a combination of a plurality of values of said monotonic function.

37. A method of forecasting strength of a structure made of concrete while hardening, the method comprising:

(a) measuring at least one physical parameter characterizing the concrete over a predetermined time-interval, so as to obtain at least one series of measurements;

(b) extracting a predetermined monotonic time-dependence of said at least one physical parameter over at least a portion of said predetermined time-interval, said predetermined monotonic time-dependence comprising a power-law function; and (c) using said predetermined time-dependence of said at least one physical parameter to forecast the strength of the concrete at a future time.

38. The method of claim 37, wherein at least one of said steps (a), (b) and (c) is performed in situ.

39. The method of claim 37, wherein said at least one physical parameter is selected from the group consisting of energy, density, sound wave velocity, electrical conductivity, electrical resistance, electrical capacitance, dielectric permittivity, heat capacity, viscosity, shear stress, plastic strength, shrinkage and any combination thereof.

40. The method of claim 37, wherein an overlap between said predetermined time-interval and a setting time-interval is from about 90 percents to about 110 percents of said setting time-interval, said setting time-interval being defined between a setting-start point of the concrete and a setting-finish point of the concrete.

41. The method of claim 37, wherein said power-law function is characterized by an exponent ranging from about 0.9 to about 1.1.

42. The method of claim 37, wherein said monotonic function has a linearity of more than about 90 percents.

43. The method of claim 37, wherein said monotonic function has a linearity of more than about 93 percents.

44. The method of claim 37, wherein said monotonic function has a linearity of more than about 95 percents.

45. The method of claim 37, wherein said step of forecasting the strength of the concrete at said future time comprises:

(i) extracting a representative quantity of said predetermined time-dependence; and (ii) expressing the strength of the concrete at said future time in terms of said representative quantity, using a predetermined forecasting function.

46. The method of claim 45, wherein said predetermined forecasting function is monotonic.

47. A method of forecasting strength of a structure made of concrete while hardening, the method comprising:

(a) measuring at least one physical parameter characterizing the concrete over a predetermined time-interval, so as to obtain at least one series of measurements;
(b) extracting a predetermined time-dependence of said at least one physical parameter over at least a portion of said predetermined time-interval; and
(c) using said predetermined time-dependence of said at least one physical parameter to forecast the strength of the concrete at a future time by:
(i) extracting a representative quantity of said predetermined time-dependence; and
(ii) expressing the strength of the concrete at said future time in terms of said representative quantity, using a predetermined monotonic forecasting function which comprises a power-law function.

48. The method of claim 47, wherein said power-law function is characterized by an exponent ranging from about 0.9 to about 1.1.

49. The method of claim 46, wherein said predetermined forecasting function is substantially linear.

50. The method of claim 45, wherein said representative quantity is dimensionless.

51. The method of claim 45, wherein said representative quantity equals a derivative of said predetermined time-dependence.

52. The method of claim 51, wherein said derivative is selected from the group consisting of a first derivative end a second derivative.

53. The method of claim 45, wherein said representative quantity equals a difference between two values of said at least one physical parameter.

54. The method of claim 50, wherein said representative quantity is a ratio between a first value of said at least one physical parameter and a second value of said at least one physical parameter, said first and said second values of said at least one physical parameter being measured at two different time points within said at least said portion of said predetermined time-interval.

55. The method of claim 45, wherein said representative quantity is a value of said monotonic function or a combination of a plurality of values of said monotonic function.

56. An apparatus for forecasting strength of a chemically active material, while hardening, the chemically active material being characterized by at least one physical parameter, the apparatus comprising:
(a) an input unit for inputting at least one series of measurements of the at least one physical parameter over a predetermined time-interval;
(b) an extractor for extracting a predetermined time-dependence of said at least one physical parameter over at least a portion of said predetermined time-interval; and
(c) a forecasting unit for forecasting the strength of the chemically active material at a future time, using said predetermined time-dependence of said at least one physical parameter, said forecasting unit comprising:
(i) a first electronic-calculation functionality for extracting a representative quantity of said predetermined time-dependence; and
(ii) a second electronic-calculation functionality for expressing the strength of the chemically active material at said future time in terms of said representative quantity, using a predetermined monotonic forecasting function which comprises a power-law function.

57. The apparatus of claim 56, wherein an overlap between said predetermined time-interval and a setting time-interval is from about 90 percents to about 110 percents of said setting time-interval, said setting time-interval being defined between a setting-start point of the chemically active material and a setting-finish point of the chemically active material.

58. The apparatus of claim 56, wherein said predetermined time-dependence comprises a monotonic function.

59. The apparatus of claim 58, wherein said monotonic function comprises a power-law function.

60. The apparatus of claim 59, wherein said power-law function is characterized by an exponent ranging from about 0.9 to about 1.1.

61. The apparatus of claim 58, wherein said monotonic function has a linearity of more than about 90 percents.

62. The apparatus of claim 58, wherein said monotonic function has a linearity of more than about 93 percents.

63. The apparatus of claim 58, wherein said monotonic function has a linearity of more than about 95 percents.

64. The apparatus of claim 56, wherein said power-law function is characterized by an exponent ranging from about 0.9 to about 1.1.

65. The apparatus of claim 56, wherein said predetermined forecasting function is substantially linear.

66. The apparatus of claim 56, wherein said representative quantity is dimensionless.

67. The apparatus of claim 56, wherein said representative quantity equals a derivative of said predetermined time-dependence.

68. The apparatus of claim 67, wherein said derivative is selected from the group consisting of a first derivative and a second derivative.

69. The apparatus of claim 56, wherein said representative quantity equals a difference between two values of said at least one physical parameter.

70. The apparatus of claim 66, wherein said representative quantity is a ratio between a first value of said at least one physical parameter and a second value of said at least one physical parameter, said first and said second values of said at least one physical parameter being measured at two different time points within said at least said portion of said predetermined time-interval.

71. The apparatus of claim 56, wherein said predetermined time-dependence comprises a monotonic function.

72. The apparatus of claim 71, wherein said representative quantity is a value of said monotonic function or a combination of a plurality of values of said monotonic function.

73. A system for forecasting strength of a chemically active material while hardening, the chemically active material being characterized by at least one physical parameter, the system comprising:
(a) a measuring device for measuring the at least one physical parameter over a predetermined time-interval, so as to obtain at least one series of measurements;
(b) an input unit for inputting said at least one series of measurements;
(c) an extractor for extracting a predetermined monotonic time-dependence of said at least one physical parameter over at least a portion of said predetermined time-interval, said predetermined monotonic time-dependence comprising a power-law function; and
(d) a forecasting unit for forecasting the strength of the chemically active material at a future time, using said predetermined time-dependence of said at least one physical parameter.

74. The system of claim 73, wherein said measuring device is selected from the group consisting of a nuclear magnetic resonance device, an acoustical device, a rheology device, an electrical device, a thermal device and any combination thereof.

75. The system of claim 73, wherein an overlap between said predetermined time-interval and a setting time-interval is from about 90 percents to about 110 percents of said setting time-interval, said setting time-interval being defined between a setting-start point of the chemically active material and a setting-finish point of the chemically active material.

76. The system of claim 73, wherein said power-law function is characterized by an exponent ranging from about 0.9 to about 1.1.

77. The system of claim 73, wherein said monotonic function has a linearity of more than about 90 percents.

78. The system of claim 73, wherein said monotonic function has a linearity of more than about 93 percents.

79. The system of claim 73, wherein said monotonic function has a linearity of more than about 95 percents.

80. The system of claim 73, wherein said forecasting unit comprises:
(i) a first electronic-calculation functionality for extracting a representative quantity of said predetermined time-dependence; and
(ii) a second electronic-calculation functionality for expressing the strength of the chemically active material at said future time in terms of said representative quantity, using a predetermined forecasting function.

81. The system of claim 80, wherein said predetermined forecasting function is monotonic.

82. The system of claim 81, wherein said predetermined forecasting function comprises a power-law function.

83. The system of claim 82, wherein said power-law function is characterized by an exponent ranging from about 0.9 to about 1.1.

84. The system of claim 81, wherein said predetermined forecasting function is substantially linear.

85. The system of claim 80, wherein said representative quantity is dimensionless.

86. The system of claim 80, wherein said representative quantity equals a derivative of said predetermined time-dependence.

87. The system of claim 86, wherein said derivative is selected from the group consisting of a first derivative and a second derivative.

88. The system of claim 80, wherein said representative quantity equals a difference between two values of said at least one physical parameter.

89. The system of claim 85, wherein said representative quantity is a ratio between a first value of said at least one physical parameter and a second value of said at least one physical parameter, said first and said second values of said at least one physical parameter being measured at two different time points within said at least said portion of said predetermined time-interval.

90. The system of claim 80, wherein said representative quantity is a value of said monotonic function or a combination of a plurality of values of said monotonic function.

91. A method of forecasting strength of a chemically active material while hardening, the chemically active material being characterized by at least one physical parameter, the method comprising:
(a) measuring the at least one physical parameter over a predetermined time-interval, so as to obtain at least one series of measurements, said measurements being selected from the group consisting of NMR measurements, acoustic measurements, calorimetric measurements and electrical measurements;
(b) extracting a predetermined time-dependence of the at least one physical parameter over at least a portion of said predetermined time-interval; and
(c) using said predetermined time-dependence of the at least one physical parameter to forecast the strength of the chemically active material at a future time by:
(i) extracting a representative quantity of said predetermined time-dependence; and
(ii) expressing the strength of the chemically active material at said future time in terms of said representative quantity, using a predetermined monotonic forecasting function which comprises a power-law function.

92. A method of forecasting strength of a chemically active material while hardening, the chemically active material being characterized by at least one physical parameter, the method comprising:
(a) measuring the at least one physical parameter over a predetermined time-interval, so as to obtain at least one series of measurements, said measurements being selected from the group consisting of NMR measurements, acoustic measurements, calorimetric measurements and electrical measurements;
(b) extracting a predetermined time-dependence of the at least one physical parameter over at least a portion of said predetermined time-interval; and
(c) using said predetermined time-dependence of the at least one physical parameter to forecast the strength of the chemically active material at a future time by:
(i) extracting a representative quantity of said predetermined time-dependence, said representative quantity being a derivative of said predetermined time-dependence; and
(ii) expressing the strength of the chemically active material at said future time in terms of said representative quantity, using a predetermined forecasting function.

93. An apparatus for forecasting strength of a chemically active material while hardening, the chemically active material being characterized by at least one physical parameter, the apparatus comprising:
(a) an input unit for inputting at least one series of measurements of the at least one physical parameter over a predetermined time-interval;
(b) an extractor for extracting a predetermined time-dependence of said at least one physical parameter over at least a portion of said predetermined time-interval; and
(c) a forecasting unit for forecasting the strength of the chemically active material at a future time, using said predetermined time-dependence of said at least one physical parameter; said forecasting unit comprising:
(i) a first electronic-calculation functionality for extracting a representative quantity of said predetermined time-dependence, said representative quantity being a derivative of said predetermined time-dependence; and
(ii) a second electronic-calculation functionality for expressing the strength of the chemically active material at said future time in terms of said representative quantity, using a predetermined forecasting function.

94. A system for forecasting strength of a chemically active material while hardening, the chemically active material being characterized by at least one physical parameter, the system comprising:
(a) a measuring device for measuring the at least one physical parameter over a predetermined time-interval, so as to obtain at least one series of measurements;

(b) an input unit for inputting said at least one series of measurements;

(c) an extractor for extracting a predetermined time-dependence of said at least one physical parameter over at least a portion of said predetermined time-interval; and (d) a forecasting unit for forecasting the strength of the chemically active material at a future time, using said predetermined time-dependence of said at least one physical parameter, said forecasting unit comprising:

(i) a first electronic-calculation functionality for extracting a representative quantity of said predetermined time-dependence; and (ii) a second electronic-calculation functionality for expressing the strength of the chemically active material at said future time in terms of said representative quantity, using a predetermined monotonic forecasting function which comprises a power-law function.

95. A system for forecasting strength of a chemically active material while hardening, the chemically active material being characterized by at least one physical parameter, the system comprising:

(a) a measuring device for measuring the at least one physical parameter over a predetermined time-interval, so as to obtain at least one series of measurements;

(b) an input unit for inputting said at least one series of measurements;

(c) an extractor for extracting a predetermined time-dependence of said at least one physical parameter over at least a portion of said predetermined time-interval; and (d) a forecasting unit for forecasting the strength of the chemically active material at a future time, using said predetermined time-dependence of said at least one physical parameter, said forecasting unit comprising:

(i) a first electronic-calculation functionality for extracting a representative quantity of said predetermined time-dependence, said representative quantity being a derivative of said predetermined time-dependence; and (ii) a second electronic-calculation functionality for expressing the strength of the chemically active material at said future time in terms of said representative quantity, using a predetermined forecasting function.

96. A system for forecasting strength of a chemically active material while hardening, the chemically active material being characterized by at least one physical parameter, the system comprising:

(a) a measuring device for measuring the at least one physical parameter over a predetermined time-interval, so as to obtain at least one series of measurements;

(b) an input unit for inputting said at least one series of measurements;

(c) an extractor for extracting a predetermined time-dependence of said at least one physical parameter over at least a portion of said predetermined time-interval; and (d) a forecasting unit for forecasting the strength of the chemically active material at a future time, using said predetermined time-dependence of said at least one physical parameter, said forecasting unit comprising:

(i) a first electronic-calculation functionality for extracting a dimensionless representative quantity of said predetermined time-dependence, said representative quantity being a ratio between a first value of said at least one physical parameter and a second value of said at least one physical parameter, said first and said second values of said at least one physical parameter being measured at two different time points within said at least said portion of said predetermined time-interval; and (ii) a second electronic-calculation functionality for expressing the strength of the chemically active material at said future time in terms of said representative quantity, using a predetermined forecasting function.

97. A system for forecasting strength of a chemically active material while hardening, the chemically active material being characterized by at least one physical parameter, the system comprising:

(a) a measuring device for measuring the at least one physical parameter over a predetermined time-interval, so as to obtain at least one series of measurements;

(b) an input unit for inputting said at least one series of measurements;

(c) an extractor for extracting a predetermined time-dependence of said at least one physical parameter over at least a portion of said predetermined time-interval, said predetermined time-dependence comprising a monotonic function; and (d) a forecasting unit for forecasting the strength of the chemically active material at a future time, using said predetermined time-dependence of said at least one physical parameter, said forecasting unit comprising:

(i) a first electronic-calculation functionality for extracting a representative quantity of said predetermined time-dependence, said representative quantity being a value of said monotonic function or a combination of a plurality of values of said monotonic function; and (ii) a second electronic-calculation functionality for expressing the strength of the chemically active material at said future time in terms of said representative quantity, using a predetermined forecasting function.

* * * * *